United States Patent
Heller

(10) Patent No.: US 9,297,763 B2
(45) Date of Patent: Mar. 29, 2016

(54) DETECTION APPARATUS AND METHOD FOR THE AUTOMATIC DETECTION OF PARTICLES

(71) Applicant: EADS Deutschland GmbH, Ottobrunn (DE)

(72) Inventor: Christoph Heller, Taufkirchen (DE)

(73) Assignee: EADS Deutschland GmbH, Ottobrunn (DE)

( * ) Notice: Subject to any disclaimer, the term of this patent is extended or adjusted under 35 U.S.C. 154(b) by 26 days.

(21) Appl. No.: 14/034,606

(22) Filed: Sep. 24, 2013

(65) Prior Publication Data

US 2014/0087389 A1  Mar. 27, 2014

(30) Foreign Application Priority Data

Sep. 24, 2012 (DE) .......................... 10 2012 108 989

(51) Int. Cl.
| | |
|---|---|
| G01N 21/64 | (2006.01) |
| C12M 1/36 | (2006.01) |
| G01N 15/14 | (2006.01) |

(52) U.S. Cl.
CPC ........ G01N 21/6486 (2013.01); G01N 15/1404 (2013.01)

(58) Field of Classification Search
CPC ................................................ G01N 21/6486
USPC ............................... 435/6.1, 7.1, 287.2, 288.7
See application file for complete search history.

(56) References Cited

U.S. PATENT DOCUMENTS

| | | | |
|---|---|---|---|
| 5,092,989 A * | 3/1992 | Steen | 210/85 |
| 2002/0086340 A1* | 7/2002 | Veerapandian et al. | 435/7.23 |
| 2002/0192113 A1 | 12/2002 | Uffenheimer et al. | |
| 2003/0190608 A1* | 10/2003 | Blackburn | 435/6 |
| 2013/0301044 A1 | 11/2013 | Friedberger et al. | |

FOREIGN PATENT DOCUMENTS

| | | |
|---|---|---|
| DE | 40 33 168 A1 | 4/1991 |
| DE | 693 23 700 T2 | 10/1999 |
| DE | 698 04 239 T2 | 10/2002 |
| DE | 10 2007 021 387 A1 | 11/2008 |
| DE | 10 2008 035 770 A1 | 2/2010 |
| DE | 10 2008 035 771 B4 | 4/2011 |
| DE | 10 2009 048 790 A1 | 4/2011 |
| DE | 10 2009 048 811 A1 | 4/2011 |
| DE | 10 2010 053 749 A1 | 6/2012 |

(Continued)

OTHER PUBLICATIONS

European Search Report for the corresponding European application No. 13 18 5599, issued on May 29, 2015.

*Primary Examiner* — Betty Forman
(74) *Attorney, Agent, or Firm* — Global IP Counselors, LLP

(57) ABSTRACT

A detection apparatus and method for the automatic detection of particles, in particular biological particles, in a sample. The detection apparatus comprises a detection device for recording the particles, and a fluidic device for automatically conveying the sample to the detection device. The fluidic device comprises a treatment device for the automatic treatment of the particles for the purpose of detection, and the detection device comprises a flow cytometer for recording at least one physical parameter of the treated particles. The detection method includes operations performed by the detection device, the fluidic device, the treatment device and the flow cytometer.

13 Claims, 4 Drawing Sheets

(56) References Cited

FOREIGN PATENT DOCUMENTS

| WO | 91/17422 A1 | 11/1991 |
| WO | WO00/20873 * | 4/2000 |
| WO | 2004/034036 A2 | 4/2004 |
| WO | 2011/042253 A1 | 4/2011 |

* cited by examiner

DETECTION APPARATUS AND METHOD FOR THE AUTOMATIC DETECTION OF PARTICLES

CROSS-REFERENCE TO RELATED APPLICATION

This application claims priority under 35 U.S.C. §119(a) to German Patent Application No. 10 2012 108 989.2, filed in Germany on Sep. 24, 2012, the entire contents of German Patent Application No. 10 2012 108 989.2 are hereby incorporated herein by reference.

BACKGROUND

1. Field of the Invention

The present invention relates to a detection apparatus and a method for the automatic detection of particles, particularly of biological particles.

2. Background Information

The detection of, for example, bacteria or other biological particles in liquid media is routinely used in monitoring the quality of, for example, drinking water, ground water or also bathing waters. The water-borne spread of, for example, epidemics can be effectively prevented by the global introduction of such routine quality checks.

Common methods for the detection of biological particles are, for example, cultivation methods in which, for instance, water samples are incubated with suitable media in order to be able to determine the type and concentration of particles in the sample subsequent to incubation. However, such known cultivation methods have a number of drawbacks because they require, in particular, a long incubation period of at least 24 hours and necessitate numerous manual steps for treating the samples and incubation media, which require experienced personnel and a special infrastructure, such as a laboratory, for example. Additionally, elements of uncertainty, for example due to manual counting, are inherent to these methods.

Therefore, it is desired that alternative devices and methods be provided with which a faster and more reliable detection of biological particles in samples is possible. In particular, devices and methods are desired that are capable of carrying out the detections automatically, i.e. largely without using trained personnel, and also outside specialized laboratories. Examples for such methods as alternatives to the known cultivation methods are disclosed in DE 10 2007 021 387 A1, in DE 10 2008 035 771 B4, DE 10 2008 035 770 A1, DE 10 2009 048 811 A1 and DE 10 2009 048 790 A1. In these above-mentioned examples, the biological particles are concentrated on filter materials in automatic processes and recorded on the filter material through automated microscopic devices.

SUMMARY

The invention is based upon the object of proposing an alternative to the above-mentioned examples with which biological particles can be automatically detected without using a filter and recorded particularly with regard to their concentration.

A detection apparatus for the automatic detection of particles, particularly of biological particles, in a sample comprises a detection device for recording the particles and a fluidic device for automatically conveying the sample to the detection device. The fluidic device comprises a treatment device for the automatic treatment of the particles for the purpose of detection, and the detection device comprises a flow cytometer for recording at least one physical parameter of the treated particles.

In a flow cytometer, particles are not concentrated on a filter material but recorded individually by measuring physical parameters of the particles, so that a determination both with respect to the type of recorded particle and with respect to the number of the particles in the sample subjected to measurement is made possible. If a sufficient number of detectable particles is contained in the sample, the concentration of the sample prior to the detection using a filter material can be dispensed with. Thus, steps for providing clean filter materials, such as cleaning or replacing steps, can also be omitted. Thus, an automatic detection of the particles is simplified.

Hitherto, however, the samples that are to be recorded in a flow cytometer were previously manually treated and also manually supplied to the detection area of the flow cytometer. Therefore, an automatic fluidic device is now being provided which automatically conveys a sample to the detection device. At the same time, the fluidic device also enables an automatic treatment of the particles present in the sample, so that they can be detected in the detection device. Thus, it is now possible to carry out the recording of the particles present in the sample according to type and concentration automatically using a flow cytometer. Therefore, no trained personnel needs to be provided which manually treats the sample and supplies it to the detection area of the flow cytometer, since both tasks are taken over by the fluidic device.

Preferably, the treatment device comprises a mixing device for automatically mixing the sample with at least one reaction fluid. In that case, the sample, or the particles contained therein, can be caused to react with the reaction fluid in the mixing device in order to render the particles detectable, preferably in the flow cytometer.

As a further advantage, the treatment device comprises at least one reservoir for storing the reaction fluid. Thus, the reaction fluid required for treating the particles in the sample can preferably be stored directly in the detection apparatus, so that it can advantageously be accessed automatically. Particularly, the treatment device also comprises a sample collecting apparatus for automatically collecting the sample.

Advantageously, it is thus also possible to automatically collect a sample and transfer it into the mixing device, so that preferably no personnel is required for taking samples. Preferably, the treatment device comprises a waste container for collecting waste fluid.

It is thus possible, for example, to dispose of the reaction fluid that is no longer required from the mixing device directly into the advantageous waste container, so that the mixing device advantageously is available for further treatment steps, for example. Preferably, the mixing device is configured as a pumping device, particularly as a continuous pumping device, for pumping, particularly continuously pumping, the sample and/or the reaction fluid and/or a mixture of sample and reaction fluid through at least a partial portion of the fluidic device. Advantageously, additional pumping devices, for example for collecting samples or for transferring a treated sample to the detection device or also for conveying reaction fluid that is no longer required to the waste container, can be dispensed with.

Preferably, the mixing device comprises a heating device for regulating the temperature of the sample and/or of the reaction fluid and/or the mixture of sample and reaction fluid. Advantageously, the reaction of particles in the sample with the reaction fluid can be promoted therewith, or even made possible at all.

In one embodiment the pumping device is configured as a plunger syringe, with a worm gear, in particular, being provided for driving the plunger. Plunger syringes are particularly easy to operate, precise with regard to dosing, and inexpensive to purchase and can advantageously be controlled very easily with regard to the volume to be handled. Additionally, mixing fluids present in the plunger syringe by moving the plunger of the plunger syringe up and down is advantageously possible, so that, advantageously, further devices causing fluids to be mixed can be dispensed with.

An advantageous worm gear driving the plunger of the plunger syringe can advantageously act at the same time as a check valve to counteract an overpressure from, for example, a pipe from which a sample is to be taken. Thus, pressure reducers in the region of the sample collecting device can advantageously be avoided. In an alternative embodiment, the pumping device comprises at least one peristaltic pump. Peristaltic pumps convey fluids by continuous rotation and simultaneous compression and release of, for example, tube devices. Since the tube in this type of fluid conveyance is usually compressed at every point in time at least one point, a possible overpressure from, for example, a pipe advantageously cannot have an effect extending up to the elements downstream from the pump. Thus, pressure reducers in the region of the sample collecting device can advantageously be avoided.

Thus, fluids, such as sample liquid or reaction fluid, can advantageously be supplied to the mixing device and the reacted mixture can, for example, be supplied, preferably continuously, to a detection device. Thus, a continuous monitoring of, for example, water pipes is advantageously possible.

In a preferred embodiment the at least one reservoir comprises a reaction fluid formed by a marker fluid, particularly a dyeing fluid, and/or by a probe fluid, particularly a fluid with antibodies and/or nucleic acid fragments and/or enzyme substrates. By using markers, the particles can advantageously be color-marked. In this case, it is particularly advantageous if, for example, dyes are used that become active only after having bonded to the particles and that can then be recorded. For example, this includes visible, fluorescent or chemiluminescent dyes. Alternatively, or also additionally, probe fluids can also be used which contain probes that preferably react specifically with the particles. Inter alia, antibodies, nucleic acid fragments or enzyme substrates are examples for such specific probes.

Preferably, the fluidic device comprises at least one multiway valve for automatically connecting the mixing device with the sample collecting device and/or the at least one reservoir and/or the detection device and/or the waste container. By means of such a multiway valve it is therefore advantageously possible to first connect the mixing device with, for example, the sample collecting device and then with the reservoir in which the reaction fluid is stored, and then with the detection device. Furthermore, the mixing device can advantageously also be connected with the waste container in order preferably to remove reaction fluid that is no longer needed from the mixing device, so that, advantageously, further reaction steps can be carried out in the mixing device. By providing a multiway valve, it is thus advantageously possible to use the mixing device for different tasks in the detection apparatus. As a further advantage, the sample collecting device comprises a switching valve for automatically switching between a sample collecting position and a detection position. It is thus possible to, also advantageously, automatically take a sample from, for example, a pipe and to thus carry out, preferably in continuous intervals, a monitoring of, for example, the water quality in a pipe.

Preferably, the detection device comprises a detection container, particularly a funnel-shaped cuvette, an excitation source, particularly a light source, in particular a laser, and a detector unit, in particular a photomultiplier. By providing, for example, a funnel-shaped cuvette through which the treated sample is conveyed, the particles disposed therein are advantageously separated so that physical parameters of the individual particles can preferably be recorded individually.

A preferred method for recording particles are optical methods, which is why it is advantageous to excite the treated particles by means of electromagnetic radiation, wherein, preferably, the scattering or absorption of the irradiated light by the particles is recorded on the opposite side by means of a detector unit. In particular, the fluidic device comprises a detection device supply portion with a sheath fluid reservoir and with a feed pipe for automatically conveying a sheath fluid from the sheath fluid reservoir to the detection device, wherein the feed pipe comprises, in particular, a compressed-air pipe and/or a peristaltic pump.

In flow cytometry, the separation of the particles in a sample is preferably supported by a fluid, a so-called sheath fluid, being conveyed along a wall portion of a detection container, so that the total diameter within the detection container is reduced. If a sample now flows centrally towards the detection container, its flow diameter is reduced further not only by flowing into the detection container, but also by the narrowing caused by the sheath fluid being reduced further (so-called hydrodynamic focusing), so that the particles advantageously separate in the sample and thus advantageously pass, in particular individually, the detection device, which is formed, for example, from an excitation source and a detector unit. If this sheath fluid is now preferably also automatically conveyed via the fluidic device to the detection container, the recording of the particles can be carried out automatically, preferably without requiring trained personnel.

The flow of the sheath fluid through the detection container can be realized, for example, by applying compressed air pressing the sheath fluid into the detection container, or by means of a peristaltic pump. The used-up sheath fluid is preferably collected in a waste container after flowing through the detection container.

Further advantageously, a recycling device for recycling waste fluid is provided, which comprises at least one filter for filtering the waste fluid, the recycling device being configured, in particular, as a connection pipe between the waste container and the detection device. Thus, for example, the waste fluid can again act as a sheath fluid after having been treated in the recycling device, whereby the maintenance-free cycle time of the detection apparatus can preferably be increased. For example, an activated carbon filter, which is capable of for example, removing probes or markers from the reaction fluid, is used for treating the waste fluid. In addition, it is advantageous to provide a pore filter having pores of a pore size of between 0.1 µm to 0.3 µm, which is preferably capable of filtering out biological particles present in the waste fluid.

Preferably, the fluidic device comprises at least one reservoir with a cleaning solution, so that the fluidic device and the detection device can advantageously be automatically cleaned or disinfected and prepared for collecting a new sample. Also preferably, the fluidic device comprises at least one reservoir with a calibrating solution, so that the correct function of the detection device can be checked in certain intervals. The calibrating solution preferably consists of a mixture of fluorescent latex or polystyrene particles of a predefined size. Preferred sizes are particles with a diameter of, for example 0.2 µm, 0.5 µm, 0.75 µm, 1.0 µm, 1.5 µm and 2.0 µm. Preferably, a control device is provided for automatically controlling the elements of the fluidic device and/or the detection device.

Thus, the fluidic device or the detection device can preferably be operated automatically without requiring trained personnel, so that, for example, an advantageously continuous monitoring, or a monitoring at least in regular intervals that is automatically controlled, of a water pipe, for example, can be realized. Advantageously, the detection apparatus comprises an evaluation device for evaluating the physical parameters of the particles recorded in the detection device. Such an evaluation device is not only capable of, for example, determining from the measured physical parameters the type and number of the particles present in the sample, but also of outputting alarm signals if the concentration of the particles exceeds a threshold value, or if particles are present which constitute a hazard, for example to health.

In a possible embodiment, the evaluation device comprises a pattern recognition unit for recognizing patterns of measured physical parameters that are plotted against each other, which, in particular, comprises a storage unit for storing known patterns and a comparing unit for comparing known and recognized patterns.

Thus, carrying out an exact recording of the number of the particles is advantageously not an absolute requirement; rather, it is advantageously possible to detect whether any contaminations are present already from a change of known patterns. This is possible, for example, in a continuous regular inspection of water pipes, because ideally, water having a constant quality is normally conducted through them and a change of such a water quality can advantageously be recognized directly by means of a change of the parameter pattern. Alternatively, however, the exact number and type of biological particles can advantageously also be determined. This is advantageous, for example, where samples of an unknown provenance are to be inspected.

A method for the automatic detection of particles, particularly biological particles, comprises the following steps:

a) automatic collection in a fluidic device of a sample with particles to be recorded;

b) automatic treatment of the sample in the fluidic device;

c) automatic conveyance of the treated sample by means of the fluidic device through a detection container, wherein a sheath fluid flowing on walls of the detection container surrounds the treated sample; and d) recording at least one physical parameter of the particles in the sample.

Advantageously, a step of automatically checking the detection device by means of a calibration solution is carried out prior to step a). Further advantageously, a step of automatically cleaning the fluidic device and the detection container is carried out subsequent to step d).

Preferably, the collection and/or the treatment of the sample and/or the conveyance of the sample through the detection container take place continuously in the process. Advantageously, the steps of detection are carried out in a detection apparatus, the elements of the detection apparatus being controlled by a control device in such a way that the steps of detection take place automatically. Preferably, several physical parameters of the particles are recorded in step d), in particular size, surface structure, intensity of fluorescence and/or wavelength of fluorescence, wherein in a step e), evaluation of the recorded parameters, either at least two of the recorded parameters are plotted against each other, with a pattern of the plot being recognized and compared with known patterns, or the particles are recorded individually.

BRIEF DESCRIPTION OF THE DRAWINGS

The invention will be explained in more detail below with reference to the attached drawings. In the drawings.

DETAILED DESCRIPTION OF EMBODIMENTS

Figure 1:
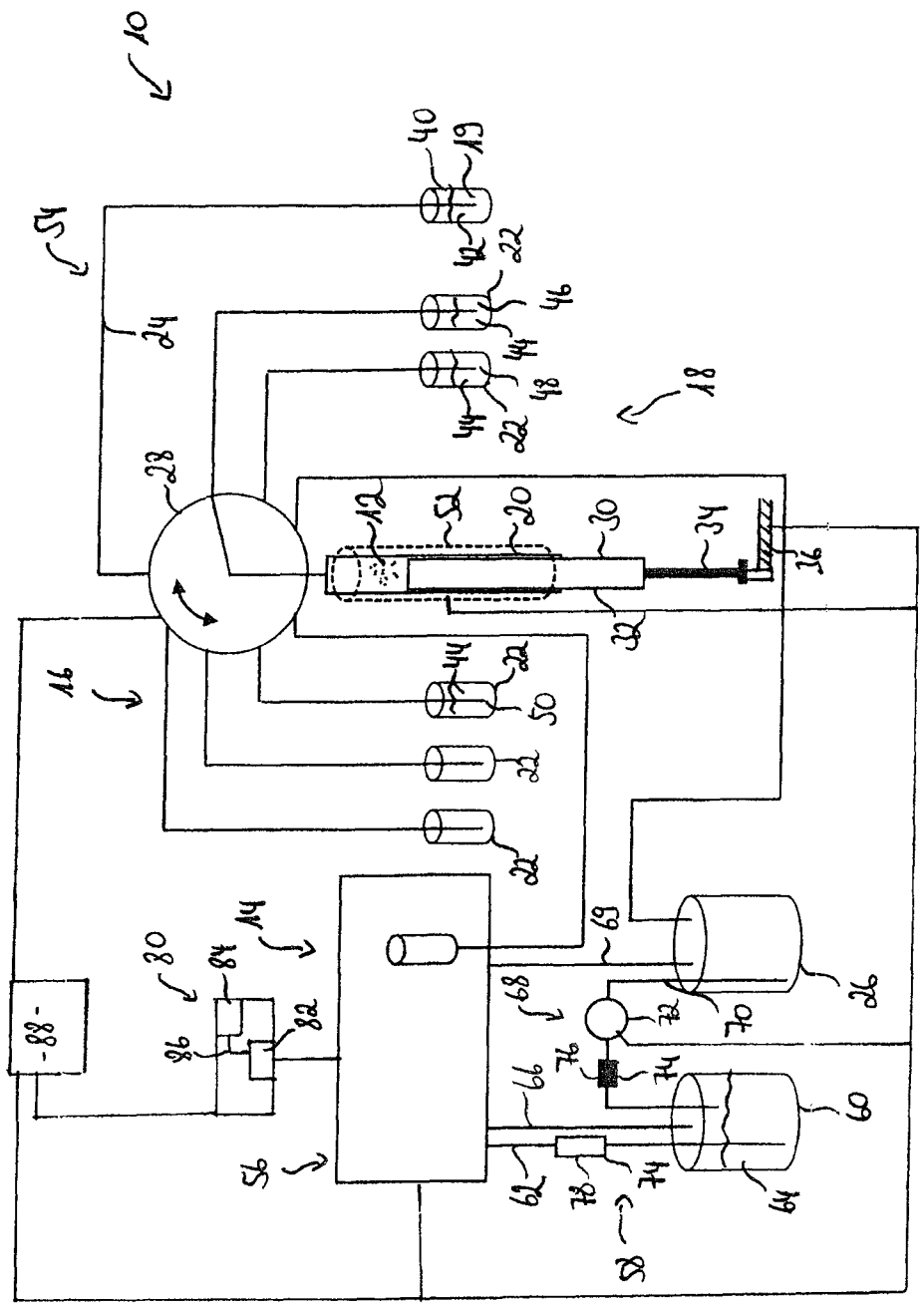
FIG. 1 shows a first embodiment of a detection apparatus for detecting biological particles.

FIG. 1 shows a detection apparatus 10 for the automatic detection of particles 12. The detection apparatus 10 comprises a detection device 14 and a fluidic device 16. The fluidic device 16 comprises a treatment device 18 in which particles 12 of a sample 19 to be tested can be treated automatically. The treatment device 18 comprises a mixing device 20, several reservoirs 22 and a sample collecting apparatus 24. In addition, a waste container 26 is provided in the treatment device 18.

Via a multiway valve 28, the mixing device 20 can be connected both to the sample collecting apparatus 24, each of the reservoirs 22, the detection device 14, as well as to the waste container 26. In the present embodiment the mixing device 20 is configured as a pumping device 30 in the form of a plunger syringe 32. In this case, a plunger 34 of the plunger syringe 32 is driven by a worm gear 36. If a sample 19 is now to be tested as to whether and in which concentration it contains, in particular, biological particles 12, the mixing device 20 is connected by means of the multiway valve 28 to the sample collecting apparatus 24, which protrudes into a sample container 40.

The plunger 34 is retracted by means of the worm gear 36, so that a negative pressure is created in the plunger syringe 32 and a sample liquid 42 is drawn from the sample container 40 into the mixing device 20. Subsequently the plunger syringe 32 is connected via the multiway valve 28 to the reservoirs 22 in order to collect reaction fluid 44 therefrom, which is mixed in the plunger syringe 32 with the sample liquid 42 by moving the plunger 34 up and down.

The reaction fluid 44 can be configured as a marker fluid 46 and contain a dye. Alternatively, or also additionally, it is possible to configure the reaction fluid 44 as a probe fluid 48 having probes for the specific reaction with the particles 12 in the sample 19.

In the present embodiment reservoirs 22 for storing washing liquid 50 are additionally provided. After the sample liquid 42 has been brought together with the reaction fluid 44 in the plunger syringe 32, a regulated heating device 52 can be switched on in order to temperature-regulate the liquid in the plunger syringe 32 and thus support or make possible at all a reaction between the markers or probes present in the reaction fluid 44 and the particles 12 in the sample liquid 42.

Subsequently the plunger syringe 32 is connected via the multiway valve 28 with the detection device 14, so that the treated sample liquid 42 can be conveyed into the detection device 14 by moving the plunger 34. Both the multiway valve 28 and the worm gear 36 are driven by stepping motors that are not shown. Excess reaction fluid 44 or washing liquid 50 can be removed from the plunger syringe 32 by connecting the plunger syringe 32 to the waste container 26.

The above-described elements of the treatment device 18 constitute a partial portion 54 of the fluidic device 16.

The detection device 14 comprises a flow cytometer 56. The treated sample liquid 42 is automatically conveyed by the fluidic device 16 from the treatment device 18 to this flow cytometer 56, so that physical parameters of the treated particles 12 can be recorded. The fluidic device 16 additionally comprises a detection device supply portion 58 which is capable of supplying the detection device 14 with fluids required therein. For this purpose, a sheath fluid reservoir 60, from which a sheath fluid 64 can be conveyed to the detection device 14 via a feed pipe 62, is provided in the detection device supply portion 58.

In flow cytometry, as is described in more detail further below, the treated sample liquid 42 is sheathed by a sheath fluid 64 in order thus to reduced the flow diameter of the sample liquid 42 and enable a separation of the treated particles 12 contained therein. In the embodiment shown in FIG. 1, the feed pipe 62 is supported by providing a compressed-air pipe 66 through which compressed air is introduced into the sheath fluid reservoir 60 in order thus to press sheath fluid 64 through the feed pipe 62.

In the present embodiment of the detection apparatus 10 a recycling device 68 is provided with which it is possible to treat waste fluid, which has been conveyed from the plunger syringe 32 into the waste container 26, and to re-use it in the detection device 14 as a sheath fluid 64. Sheath fluid 64 used in the detection device 14 or tested sample liquid 42 is also introduced into the waste container 26 via a discharge pipe 69 and can thus be reused. For recycling, the waste container 26 is connected via a connection pipe 70 to the sheath fluid reservoir 60 and thus to the detection device 14.

A pump 72 for pumping the waste fluid into the sheath fluid reservoir 60 and a filter 74 in the form of an activated carbon filter 76 are disposed in the connection pipe 70. Marker molecules or probe molecules that are possibly present in the waste fluid can be filtered out by the activated carbon filter 76.

Furthermore, the feed pipe 78 also comprises a filter 74 in the form of a pore filter 78 by means of which biological particles 12 or other contaminations that are possibly present in the waste fluid can be filtered out. For this purpose, the pore filter 78 preferably has pores with a pore size of between 0.1 µm to 0.3 µm, which is an order of magnitude smaller than, in particular, bacteria.

The fluidic device 16 comprises at least one container 22 with cleaning liquid, so that after the completion of detection of a sample 19, all of the pipes can be automatically emptied, cleaned and refilled. This prevents contaminations and carry-overs. Moreover, the fluidic device 16 is capable of automatically diluting samples 19 with a high number of particles 12. Depending on the characteristics of the detectors and the flow speeds of the sheath fluid 64 and the sample liquid 42, the recording of a high number of particles 12 is limited. This is the case particularly if the number of particles 12 is so large that they cannot be separated in the detection device 14 any longer, but that several particles 12 are recorded as a single one. In this case, a dilution of the sample 19 with pure fluid is required, which can also be accomplished by the fluidic device 16.

After recording the physical parameters of the treated particles 12 in the detection device 14, the recorded data are evaluated in an evaluation device 80. The evaluation device 80 comprises a pattern recognition unit 82 including a storage unit 84 as well as a comparing unit 86.

If several physical parameters of the treated particles 12 are recorded in the detection device 14, they can advantageously be plotted against each other into a pattern. Such patterns can be recognized in the pattern recognition unit 82 by, for example, a known pattern stored in the storage unit 84 being compared with a recorded pattern by the comparing unit 86. If there are deviations in the pattern, this suggests that the sample 19 is contaminated. If there are no known patterns for a measured sample 19 in the storage unit 84, it is alternatively possible to record the particles 12 individually according to their type and concentration in the sample 19.

The detection apparatus 10 comprises a control device 88, by means of which all of the elements of the detection apparatus 10, particularly all elements of the fluidic device 16 and of the detection device 14, can be controlled automatically. Thus, trained personnel is required neither for taking samples, nor for treating the sample 19, nor for detection, nor for evaluation.

Figure 2:
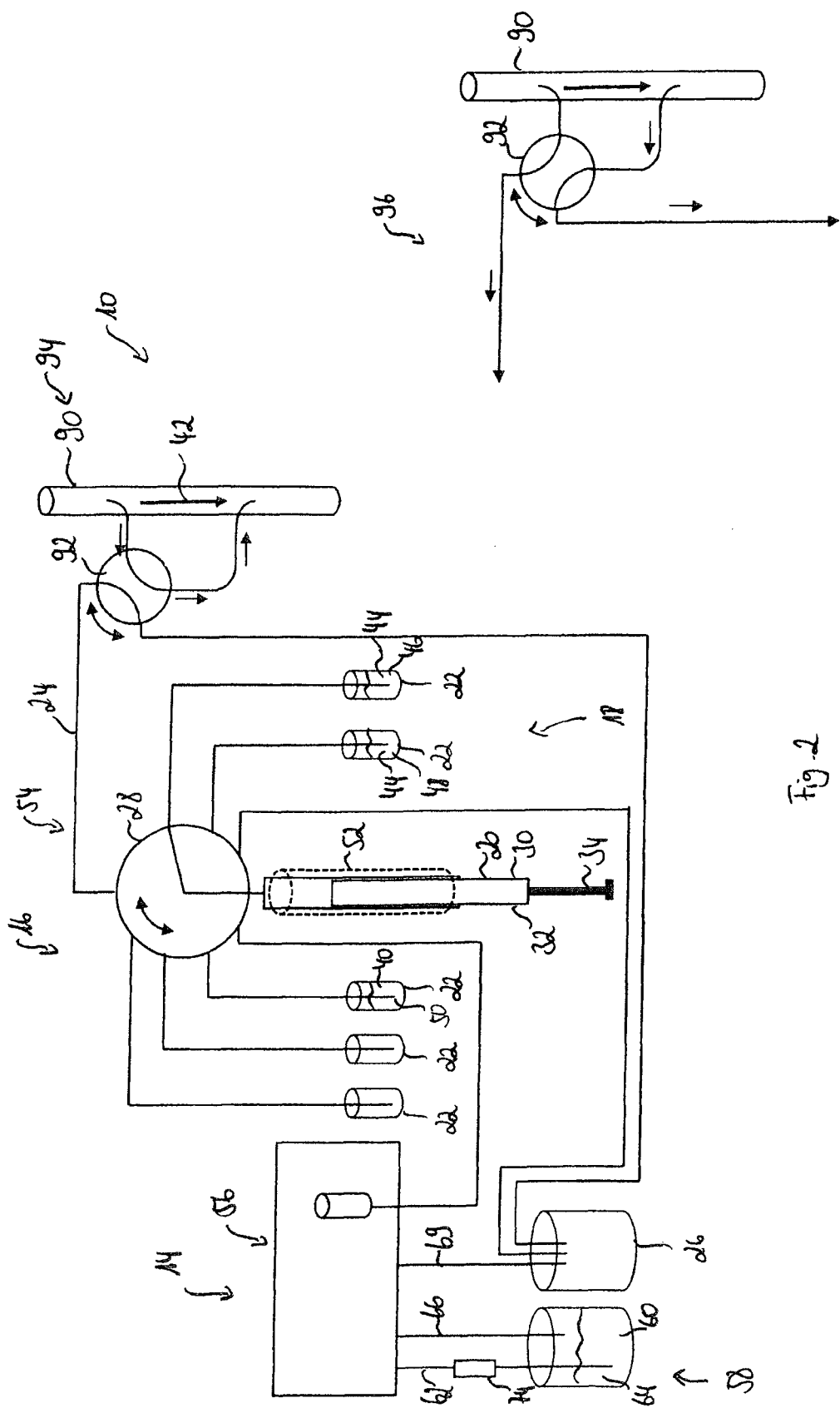
FIG. 2 shows a modified first embodiment of the detection apparatus from FIG. 1, wherein an automatic taking of a sample from a pipe is possible.

FIG. 2 shows a modified detection apparatus 10, which is largely identical to the detection apparatus 10 in FIG. 1, with only the sample collecting apparatus 24 being altered. The recycling device 68 can also be provided but is not shown in FIG. 2 for reasons of clarity.

The altered sample collecting apparatus 24 in FIG. 2 is modified in such a way that the sample 19 can be taken directly from a pipe 90. For this purpose, the sample collecting apparatus 24 comprises a switching valve 92 which is shown both in the detection position 94 as well as in the sample collecting position 96 in FIG. 2.

In the sample collecting position 96, the switching valve 92 connects the sample collecting apparatus 24 with the pipe 90 so that a fluid, for example water, flowing in the pipe 90 is introduced directly into the sample collecting apparatus 24. For this purpose, the presence of the worm gear 36 on the plunger 34 is advantageous because the worm gear is irreversible and prevents a backstroke of the plunger 34 in the case of high pressures of the fluid in the pipe 90 during the connection of the plunger syringe 32 to the sample collecting apparatus 24.

In the detection position 94, the connection between the pipe 90 and the sample collecting apparatus 24 is interrupted, and the fluid branched off from the pipe 90 is conveyed directly back into the pipe 90. Thus, a fully automatic taking of samples from a pipe 90 that is to be monitored regularly, for example a water pipe, is possible. The detection position 94 at the same time constitutes the rest position, i.e. when there is no collection taking place. The special design of the sample collecting apparatus 24 with a 2/2-way valve ensures that all the pipes 90 are permanently flushed through with fluid and that there are no pipes 90 with stagnant fluid. Stagnant fluid would promote the formation of biofilm in the sample-taking pipes, which would lead to the measurement result being distorted.

In the detection or rest position 94, the branch-off from the main pipeline is permanently flushed through with fluid. The sample collecting pipe 24 can be automatically cleaned or disinfected by the fluidic device 16 by means of cleaning fluid.

In the sample collecting position 96, a portion of the branch-off is flushed through by the fluid sample, whereas the other portion is flushed back into the waste container 26 from the main pipe. In this way all of the elements of the sample taking system that come into contact with the sample are permanently flushed through or automatically disinfectable.

Figure 3:
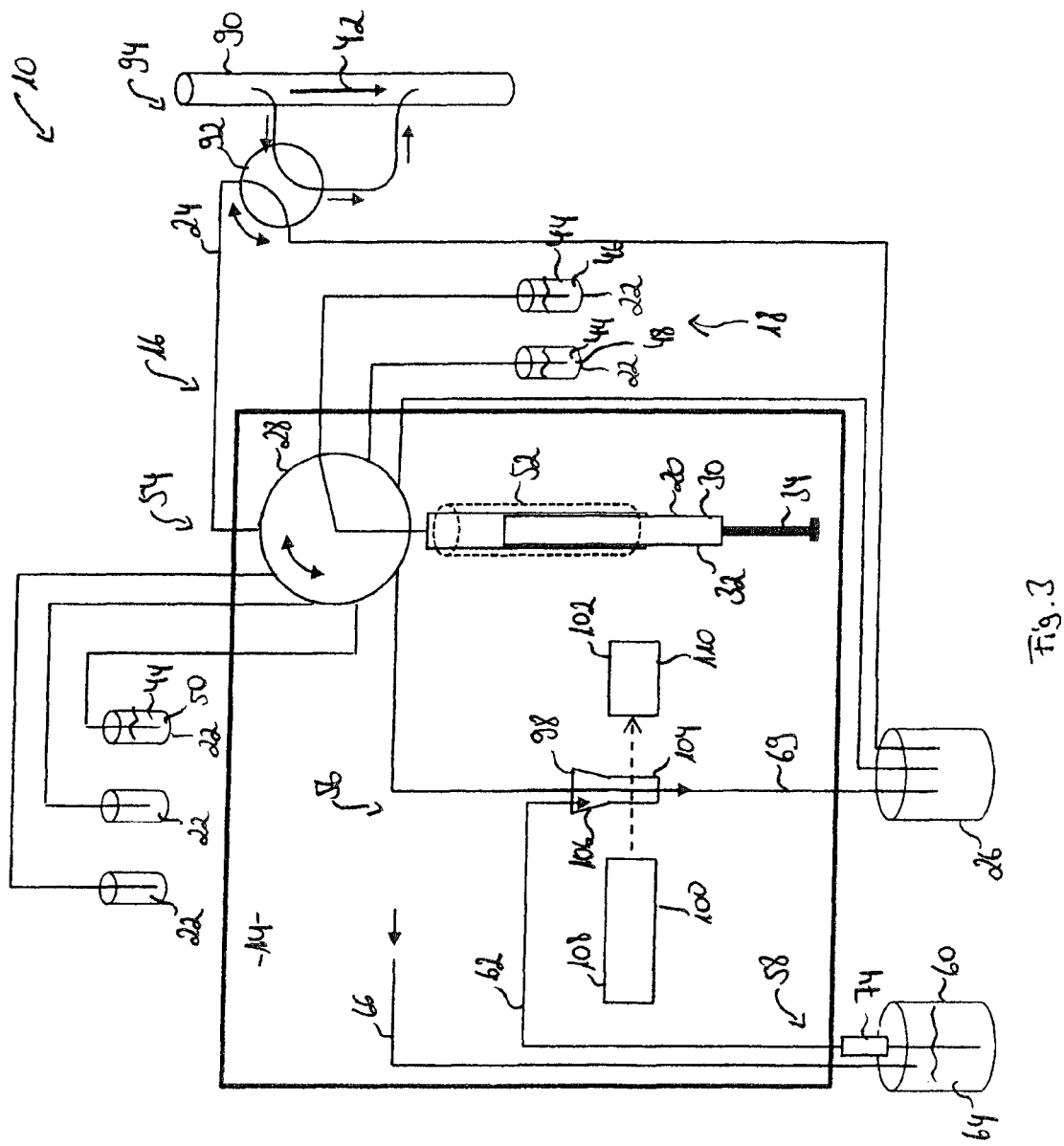
FIG. 3 shows another modified first embodiment of the detection apparatus from FIG. 1.

FIG. 3 shows another modification of the detection apparatus 10 from FIG. 1. In this case, the multiway valve 28 as well as the plunger syringe 32 is disposed directly in the detection device 14. Thus, using the pumping function of the plunger syringe 32, the treated sample liquid 42 can be directly conveyed into a detection container 98 without further pumps within the detection device 14 being required. The partial portion 54 of the fluidic device 16 described in FIG. 1 corresponds to the structure already described, with an automatic taking of samples from the pipe 90 being realized.

The detection device 14 is configured as a flow cytometer 56 and therefore comprises an excitation source 100 as well as a detector unit 102 in addition to the detection container 98. The detection container 98 is configured as a funnel-shaped cuvette 104 in order thus to reduce the flow diameter of the introduced sample liquid 42 in the flow direction. Furthermore, sheath fluid 64 is introduced via the feed pipe 62 into the cuvette 104 and guided along walls 106 of the cuvette 104. Thus, the possible flow diameter of the sample liquid 42 is reduced even more, so that particles 12 can ideally be guided past the excitation source 100 and the detector unit 102 and recorded individually.

In the present embodiment, the excitation source 100 is formed by a light source 108 in the form of a laser, and the detector unit 102 by a photomultiplier 110. The recycling device 68 can also be provided, but is not shown in FIG. 3 for reasons of clarity.

Figure 4:
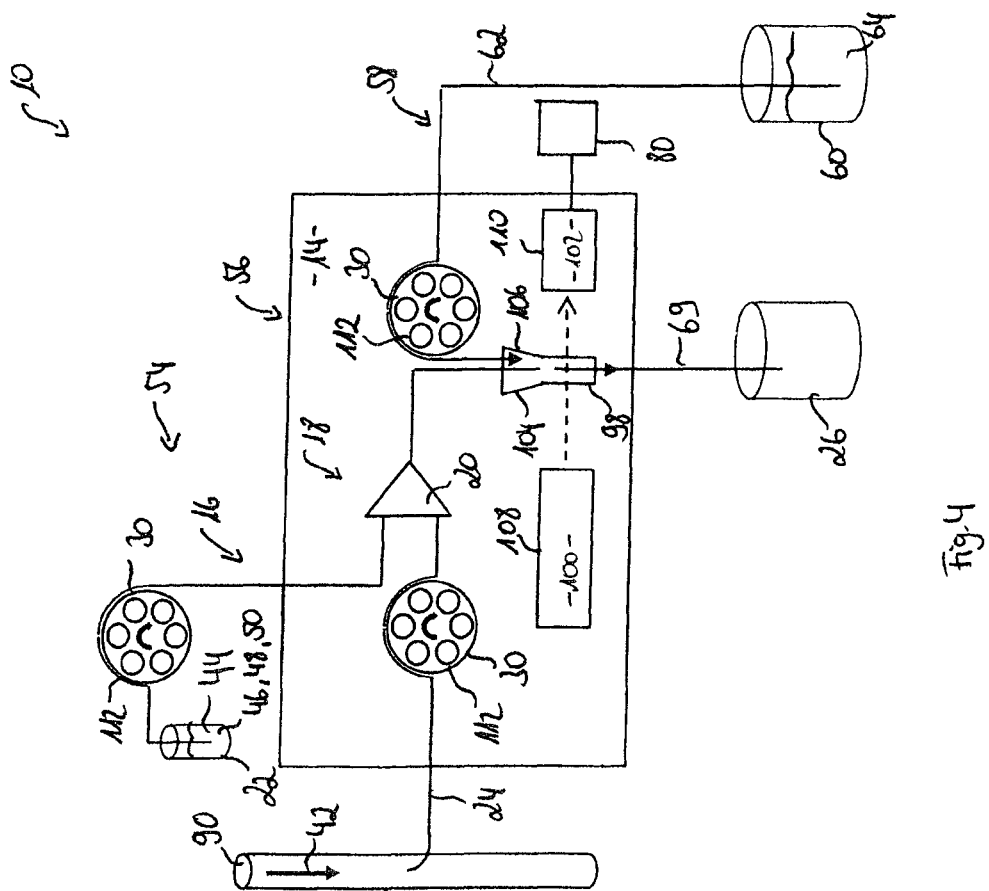
FIG. 4 shows a second embodiment of the detection apparatus for detecting biological particles.

FIG. 4 shows a second embodiment of the detection apparatus 10, which differs from the detection apparatus 10 shown in FIG. 1 to FIG. 3. Because peristaltic pumps 112 are being used in this case, which are disposed in the sample collecting apparatus 24 and between the reservoir 22 for the reaction fluid 44 and the mixing device 20. Furthermore, a peristaltic pump 112 is also provided in the feed pipe 62 from the sheath fluid reservoir 60 to the detection container 98. The peristaltic pumps 112 enable a continuous feed of sample liquid 42 or reaction fluid 44 to the mixing device 20. The prepared sample 19 is then fed to the detection container 98. By suitably selecting tube diameters and pumping speeds, the optimum mixing ratio of sample liquid 42 to reaction fluid 44 can be set.

By means of another peristaltic pump 112, a continuous feed of sheath fluid 64 as well as treated sample liquid 42 to the detection container 98 is also possible. Conveying the sheath fluid 64 is also possible through pressurization instead of by means of a peristaltic pump 112. Thus, an actual continuous monitoring of the fluid flowing in the pipe 90 is possible by means of the assembly shown in FIG. 4.

The detection apparatus 10 can be installed, for example, during the manufacture of aircraft in order to be able to be used long-term in monitoring the drinking water quality in the aircraft. For over 100 years, the determination of the hygienic quality (germ count) of for example, a water sample (drinking, bathing, mineral, surface, process water) or of beverages has been taking place by means of cultivation on nutrient-containing media, such as, for example, agar plates. This method is time-consuming, since it requires several days, indirect, not very sensitive, and requires a number of manual steps as well as specialized personnel. In contrast, a fully automatic and continuous counting of the bacteria actually contained in the sample 19, both in individual samples as well as directly on a water pipe 90, is made possible by the above-described detection apparatus 10.

As the actual detection method, the overall system contains the so-called flow cytometry. This has been known for approximately 50 years and has continuously been developed further. So far, only individual samples 19 can be analyzed with flow cytometry, and a continuous or quasi-continuous analysis is hitherto not possible with flow cytometry. This problem is now solved by a fluidic structure consisting of valve(s) and pump(s). The water sample, cleaning and buffering substances as well as suitable fluorescent probes are conveyed, mixed and temperature-regulated with the structure. Various configurations of such a structure are shown in FIG. 1 to FIG. 4 as discussed above.

The detection apparatus 10 enables an automated, quasi-continuous analysis of the hygienic quality of a water sample or another aqueous liquid (e.g. in time intervals of 10-15 minutes or shorter, depending on the reaction rate probe—sample 19). For example, an automatic and continuous counting of bacteria in water or aqueous solutions can be carried out. The detection of bacteria in water (drinking water, bathing water, mineral water, process water, surface water, ground water, waste water, cooling water, etc.), beverages (e.g. milk) or other aqueous media is routinely carried out using so-called cultivation methods. In the process, a certain quantity of the sample 19, e.g. water, is filtered and the filter is subsequently incubated with a suitable medium on an agar plate. Given high germ concentrations, a certain quantity of the sample 19 can also be put directly onto the agar plate. Various variations of this method for the specific and unspecific detection of germs were developed towards the end of the 19th century and since then used routinely in an almost unchanged form. It was possible to effectively prevent the water-borne spread of epidemics, particularly in the industrial countries, by introducing such analyses globally. Even though the cultivation method is rather old, it fulfils its purpose on a day-to-day basis, which is demonstrated by the high quality of our drinking and bathing water.

However, cultivation methods have a number of drawbacks, in particular, alot of time is required: first results after 24-48 hours; final result after 72 hours or later; cannot be automated; many manual steps (filtration, plating, counting); high degree of uncertainty or variance due to manual counting; experienced personnel required; sceptible to errors (e.g. wrong agar temperature, non-sterile work, false interpretation of the colonies); bacteria are recorded only indirectly (colonies, not individual bacteria, are being counted); low sensitivity, since only a fraction of the bacteria is recorded; small measuring range per plate (minimum approx. 30 to maximum approx. 300 colonies) and therefore, depending on the sample, corresponding dilution or concentration is required; and special infrastructure (laboratory) required.

This presents a multitude of situations or applications in which a monitoring of the hygienic quality would be urgently required, but where the cultivation method is unsuitable. This is the case particularly in time-critical processes, or also in the case of long transport distances from the location where the sample is taken to the laboratory (according to DIN EN ISO 19458, sample transport must not take any longer than 8 hours and should take place cooled, if possible). Situations of this type can be (by way of example): speedy inspection and release of water-carrying systems (pipelines, tanks) after disinfection measures; final inspection of drinking water tanks in aircraft engineering; inspection of water-carrying systems in vehicles and means of transportation with a long travel time or autonomy time (ships, submarines, aircraft, space capsules, space stations); release of products in pharmaceutical, biotech, chemical and food companies; continuous monitoring of drinking water treatment systems; continuous monitoring of water producing systems (e.g. fuel cell); detection of gradual but rapid (within 1 day) changes of water quality, e.g. by the detachment of biofilm from pipelines or contamination of the water by pipe ruptures; and detection of very rapid (within 1 hour) changes of water quality, e.g. by natural catastrophes (earthquake, torrential rain), failures and breakdowns (rupture of filters), accidents or intentional contamination (bioterrorism).

In these cases alternative, i.e. more rapid and/or automatic and/or laboratory-independent, methods for determining the hygienic quality of the water or of the liquid concerned are required. In addition to liquids, other substances and media (e.g. air, surfaces, soil samples, filter elements, solid foodstuffs, etc.) frequently have to be inspected with regard to their hygienic state. In many cases it is difficult to do so in a direct way. Rather, it is most frequently necessary and sensible to at first transfer the germs present into an aqueous medium quantitatively, if possible, and then to analyze them therein.

The following methods for transferring germs from a non-aqueous medium into an aqueous medium are common (by way of example): air sampling in aqueous medium by means of impingement, cyclone, bubbling, etc; air sampling on gelatin filter with subsequent liquefaction; swabs of surfaces and transfer into aqueous medium; dissolution of soil samples in aqueous medium; and mashing of foodstuffs.

The liquids obtained therefrom are then also tested by means of cultivation methods. However, a large number of situations arises also in this case in which a significantly faster analysis would be urgently required, for example: air quality monitoring in the military field (barracks, camps, ships, etc.) and in the case of critical infrastructures (airports, railroad stations, subways, etc.); hygienic inspection of operating rooms and intensive care units; prevention of the spread of epidemics by monitoring the air in aircraft, high-speed trains, etc.; food inspection; and monitoring of stables.

In the past years several alternatives, i.e. primarily faster methods, were developed to be able to analyze bacteria in water. As in virtually all bioanalytic methods, the following general principle is applied:

i) Reaction of the analyte (in this case: bacteria) with a "marker" or "probe. This can be, for example, an antibody, a nucleic acid fragment, an enzyme substrate or a dye. The probe itself carries a label, e.g. a dye, or produces a label (dye, electrochemical signal, etc.). Such "probes" whose labels become active only after forming the bond to the analyte are ideal. Usually, visible, fluorescent or chemiluminescent dyes are used. This step is the actual biochemical detection, or detection by means of molecular biology, and generally constitutes the limiting factor in the sensitive detection of an analyte. Therefore, particular care has to be taken in this regard, because primarily the sensitivity and specificity of the detection method depend decisively on the quality of the biological detection. The correct choice of this detection ("assay") is determined by the aim of the method (what do I want to detect?, how quickly?, etc.). An important factor in practice in detecting very small analyte quantities are the background signals due to unspecific reactions or bonds. They must be prevented or reversed. In part, they can also be excluded during the detection method.

ii) Detection of the label. Physical-technical methods are used for the subsequent or simultaneous detection of the label. The spectrum of such detection technologies ranges from electrochemical methods (voltammetry, amperometry) over radioactive detections to mass spectrometry. Optical methods, however, are the most widespread. In this case, it is advantageous if the biological detection and the detection method are closely co-ordinated.

The alternative methods for the detection of bacteria are currently also only used in the laboratory and are therefore virtually stationary. The reason for this is the size and sensitivity of the detection systems, the required storage of chemicals, required manual analysis steps, etc. A continuous measurement is also not possible. The principle of flow cytometry lies in the so-called "hydrodynamic focusing". A liquid sample 19 is pumped through a funnel-shaped cuvette 104. In the process it is sheathed by another, also pumped, liquid ("sheathing flow"), whereby the sample flow is narrowed. Both flows are laminar; the degree of the focusing of the sample flow depends on the ratio of the two pumping speeds. The sample flow, which is narrowed to a few micrometers, is guided past a detector. Given a suitable sample speed and suitable analyte concentration, the particles 12 (in this case: bacteria) present in the sample are successively guided past the detector and can thus be recorded individually. The detection unit most frequently consists of one or more lasers for illumination and three or more detectors (photomultiplier 110) for recording scattered light (towards the front and to the sides) and fluorescent signals.

The use of flow cytometry for the detection of bacteria was already described in the 1990s; however, this method was not widely used in microbiology. In the meantime, however, the instruments became less expensive, more compact and easier to operate. By using solid state lasers, they are more rugged and easier to transport. Above all, however, it was possible to reduce the spatial optical resolution to less than 1 µm, which makes the reliable recording of virtually all bacteria possible.

Flow cytometry as a detection technology for the detection of bacteria in liquids offers the following advantages: The principle of continuous sample flow renders it almost ideal for continuous measurement. Due to multiple information on the individual recorded particle 12 (the scattering of light can serve as a measure for the size; in addition, the intensity of fluorescence and of wavelength are recorded), background signals can be excluded well. The measurement is fast (1 ml of sample 19 can be analyzed in a few minutes). Because the cuvette 104 has a diameter of typically 100 ml or more, samples 19 containing large particles 12 can also be analyzed without any clogging of the detection chamber. Small-pore prefilters that would possibly cause the sample 19 to be adulterated are therefore not required.

Different configurations are possible for the automated detection of bacteria by means of flow cytometry. For automating the dyeing reaction (reaction with the labeled probe), the following concept shown in FIG. 1 was developed: the water sample and necessary further solutions are drawn up or discharged by means of a syringe pump. In this case selection takes place via a multiway selector valve. The dye is added to the water sample, incubated for a certain amount of time, and then transferred into the flow cytometer. The syringe pump itself can be heated, so that incubations at temperatures higher than room temperature are also possible. At the same time, liquids (e.g. sample 19 and dye) can be mixed through by moving the syringe plunger up and down. Diluting the water sample (in the case of heavily contaminated samples) is also possible using a pump. Coupling to the flow cytometer is effected by means of a modified sample container. Pumps and valves are driven by stepping motors.

In order to extend the autonomy of the system as regards time, the waste liquid ("waste") can be recycled through an activated carbon filter 76 and fed to the sheathing flow reservoir. In the process, the activated carbon removes the excess dye molecules (probe) from the waste liquid. Bacteria and particles are removed by an in-line filter with a pore size of approximately 0.2 µm.

By including an additional switching valve 92 (4/2-way valve), shown in FIG. 2, the entire system can be connected to a piping system ("on-line" measurement). Because the plunger 34 of the syringe pump is driven by a stepping motor via a gear worm, it is virtually impossible to move this plunger 34 by external influences. Thus, the syringe pump is unaffected by the water pressure in the pipeline so that, for example, a pressure reducer or the like is unnecessary.

The switching valve 92 is shown in FIG. 2 in the measuring position and in the injection position. Some flow cytometers internally also use a syringe pump in order to introduce the sample into the cytometer cuvette. The configuration shown in FIG. 1 and FIG. 2 can therefore also be integrated into the instrument, whereby a syringe pump is saved.

Other flow cytometers use flexible tube pumps (peristaltic pumps 112) instead of a syringe pump in order to convey the sample 19 and the sheathing flow. A genuine continuous on-line measurement can be realized using such instruments. The mixing ratio of the probe (detection reagent) to the water sample can be set through the pumping rate of the two peristaltic pumps 112. The peristaltic pumps 112 are also independent of the liquid pressure, so that a pressure reducer can also be omitted. Washing solutions, preservative solutions, detection reagents, probes such as dyes or enzyme substrates, or also beads for calibration can be used as reaction fluids 44.

In flow cytometers, the data of the optical detectors (corresponding to the individual parameters) are usually successively stored in a table (so-called "listmode data file") for each so-called "event" (recognized particle 12). Histograms can be prepared for each parameter from these tabulated raw data. However, histograms from the combination of two parameters, so-called dotplots, or even three-dimensional representations, are most frequently more informative.

Depending on the optical properties and the homogeneity of the bacteria population, different "clusters" can often be discerned in such representations. Furthermore, a differentiation between bacteria and background particles is generally also possible in this case.

In particular, in the case of source water, the composition of the bacteria population as well as the number of the abiotic particles hardly changes, not even over longer periods of time. The above-mentioned clusters therefore form a pattern typical for the respective water source. Thus, algorithms for pattern recognition are an option for information processing, so that a so-called "fingerprint" for the respective water source can be prepared. Once this pattern changes significantly, this suggests a possible germ contamination or other undesired change. In this way, the automatic, continuously measuring on-line system can be used primarily as a warning system or as a "trigger" for further tests.

If the source of the sample 19 to be tested is changed frequently, of if it is unknown (i.e. primarily in the case of off-line measurements), no fingerprint can be prepared. In this case, the pure number of recognized bacteria must be used. In this case, a "traffic light system" suggests itself for warning, with, for example, green indicating a very low number of bacteria, and red, in contrast, indicating a high number potentially dangerous to humans, which leads to an immediate ban on the water (or on the product) (action limits). A bacteria concentration in the intermediate range is represented, for example, by yellow, which symbolizes a still-harmless quantity, with, however, a second measurement potentially being indicated (warning limit).

While only selected embodiments have been chosen to illustrate the present invention, it will be apparent to those skilled in the art from this disclosure that various changes and modifications can be made herein without departing from the scope of the invention as defined in the appended claims. For example, the size, shape, location or orientation of the various components can be changed as needed and/or desired. Components that are shown directly connected or contacting each other can have intermediate structures disposed between them. The functions of one element can be performed by two, and vice versa. The structures and functions of one embodiment can be adopted in another embodiment. It is not necessary for all advantages to be present in a particular embodiment at the same time. Every feature which is unique from the prior art, alone or in combination with other features, also should be considered a separate description of further inventions by the applicant, including the structural and/or functional concepts embodied by such feature(s). Thus, the foregoing descriptions of the embodiments according to the present invention are provided for illustration only, and not for the purpose of limiting the invention as defined by the appended claims and their equivalents.

What is claimed is:

1. A detection apparatus for the automatic detection of particles in a sample, the detection apparatus comprising:
   a detector; and
   a fluidic system configured to automatically convey the sample to the detector, the fluidic system comprising
      a treatment system configured to automatically treat the particles for the purpose of detection;
      a first switching valve configured to switch between a first position in which the first switching valve directs the sample from a conduit through which a fluid containing the sample is flowing through the first switching valve and to the detector, and a second position in which the first switching valve directs the sample from the conduit through the first switching valve and back to the conduit;
      a first switch conduit configured to direct the sample from the conduit to the first switching valve; and
      a second switch conduit configured to direct the sample from the first switching valve to the conduit;
      the first switching valve being configured in the first position to direct the sample received from the first switch conduit through the first switching valve and to the detector, and being configured in the second position to direct the sample received from the first switch conduit through the first switching valve and to the second switch conduit for return back to the conduit; and
   the detector comprises a flow cytometer configured to record at least one physical parameter of the treated particles.

2. The detection apparatus according to claim 1, wherein the treatment system comprises at least one of the following:
   a mixer configured to automatically mix the sample with at least one reaction fluid;
   at least one reservoir configured to store the reaction fluid;
   a sample collector configured to automatically collect the sample; and
   a waste container configured to collect waste fluid.

3. The detection apparatus according to claim 1, wherein the treatment system comprises a mixer having at least one of the following characteristics
   the mixer is configured as a pump that is configured to pump at least one of the following
      the sample;
      the reaction fluid; and
      a mixture of the sample and the reaction fluid through at least a partial portion of the fluidic system; and
   the mixer comprises a heating device configured to regulate at least one of the temperature of the sample; the temperature of the reaction fluid; and the temperature of the mixture.

4. The detection apparatus according to claim 3, wherein the pump is configured as at least one of the following
the pump is configured as a plunger syringe having a worm gear being configured to drive the plunger; and
the pump comprises at least one peristaltic pump.

5. The detection apparatus according to claim 1, wherein the treatment system comprises at least one reservoir comprising at least one of the following
a reaction fluid formed by at least one of the following
a marker fluid; and
a probe fluid with at least one of antibodies, nucleic acid fragments and enzyme substrates.

6. The detection apparatus according to claim 2, wherein at least one of the following
the fluidic system comprises at least one multiway valve configured to automatically connect the mixer with at least one of the sample collector, at least one reservoir, the detector and the waste container; and
the sample collector comprises a second switching valve configured to automatically switch between a sample collecting position and a detection position.

7. The detection apparatus according to claim 1, wherein the detector comprises a detection container, an excitation source, and a detector unit.

8. The detection apparatus according to claim 1, wherein the fluidic system comprises a detection device supply portion with a sheath fluid reservoir and with a feed pipe configured to automatically convey a sheath fluid from the sheath fluid reservoir to the detector, the feed pipe comprising at least one of a compressed-air pipe and a peristaltic pump.

9. The detection apparatus according to claim 1, further comprising
a recycler configured to recycle waste fluid, the recycler comprises at least one filter configured to filter the waste fluid, the recycler being configured as a connection pipe between the waste container and the detector, and the filter comprises at least one of an activated carbon filter and a pore filter having pores of a pore size of between 0.1 µm to 0.3 µm.

10. The detection apparatus according to claim 1, further comprising
a controller configured to automatically control at least one of the elements of the fluidic system and the detector, the controller comprising an evaluator configured to evaluate the physical parameters of the particles recorded in the detector.

11. The detection apparatus according to claim 10, wherein the evaluator comprises a pattern recognizer configured to recognize patterns of measured physical parameters that are plotted against each other, the evaluator comprising a storage configured to store known patterns and a comparator configured to compare known and recognized patterns.

12. The detection apparatus according to claim 1, wherein the treatment system comprises at least one reservoir comprising a reaction fluid formed by at least one of the following
a marker fluid; and
a probe fluid with at least one of antibodies, nucleic acid fragments and enzyme substrates.

13. The detection apparatus according to claim 3, wherein at least one of the following
the fluidic system comprises at least one multiway valve configured to automatically connect the mixer with at least one of the sample collector, at least one reservoir, the detector and the waste container; and
the sample collector comprises a second switching valve configured to automatically switch between a sample collecting position and a detection position.

* * * * *